United States Patent [19]

Tolbert et al.

[11] 4,229,532

[45] Oct. 21, 1980

[54] PRODUCTION OF TUMOR ANGIOGENESIS FACTOR BY CELL CULTURE

[75] Inventors: William R. Tolbert, Manchester; Joseph Feder, University City, both of Mo.

[73] Assignee: Monsanto Company, St. Louis, Mo.

[21] Appl. No.: 974,406

[22] Filed: Dec. 29, 1978

[51] Int. Cl.² ............................................. C12P 1/00
[52] U.S. Cl. ...................................... 435/41; 435/68; 435/241; 435/811; 435/948; 424/95
[58] Field of Search ........................... 195/1, 1.7, 1.8; 435/41, 68, 241

[56] References Cited

U.S. PATENT DOCUMENTS

| | | | |
|---|---|---|---|
| 4,059,485 | 11/1977 | Tolbert | 195/1.8 |
| 4,059,486 | 11/1977 | Tolbert | 195/1.8 |

OTHER PUBLICATIONS

Billiau et al., Antimicrob. Agents Chemothr. 12, (1), 11–15 (1977).
Folkman et al., Fundamental Aspects of Neoplasia, pp. 401–412, Springer-Verlag, N.Y., (1975).
Folkman et al., J. Exptl. Med. 133, 275–288 (1971).
Phillips et al., Int. J. Cancer 17, 549–558 (1976).
Hubler et al., Cancer 38, 187–192 (1976).

*Primary Examiner*—Alvin E. Tanenholtz
*Attorney, Agent, or Firm*—Scott J. Meyer; James W. Williams, Jr.

[57] ABSTRACT

Process for the production of human TAF in vitro comprising growing the human osteosarcoma cell line MG-63 in agitated, liquid suspension of nutrient culture medium at about 35°–38° C. for a sufficient time to elaborate TAF and recovering the resulting TAF from the cells or cell product.

6 Claims, No Drawings

PRODUCTION OF TUMOR ANGIOGENESIS FACTOR BY CELL CULTURE

BACKGROUND OF THE INVENTION

This invention relates to the in vitro production of human tumor angiogenesis factor from the human osteosarcoma cell line MG-63.

It has been known for some time that unless a solid tumor is provided with blood vessels by its host it remains small and dormant. The substance that is released by tumors and provides vascularization has been named tumor angiogenesis factor (TAF) by Dr. Judah Folkman of the Harvard Medical School. *J. Exptl. Med.* 133, 275–88 (1971); *Cancer Res.* 34, 2109–13 (1974).

Ever since it was recognized that tumor induced neovascularization represents the breaching of an important barrier in the control of tumor growth, considerable effort has been spent in searching for ways to inhibit neovascularization. It was early suggested by Dr. Folkman that blockade of this factor (inhibition of angiogenesis) might arrest solid tumors at a tiny diameter of a few millimeters (avascular phase). *New Engl. J. Med.* 285, 1182 (1971); *J. Exptl. Med.* 133, 275–88 (1971). One suggested approach was the raising of antibodies against TAF extracts for the production of an anti-serum. Folkman, *Ann Surg.* 175, 409–16 (1972); Phillips et al., *Int. J. Cancer* 17, 549–58 (1976). Another approach to inhibiting neovascularization which has received much attention recently consists in treatment of tumor cells with extracts of cartilage. Eisenstein et al, *Am. J. Pathol.* 73, 765–74 (1973); Sorgente et al., *Lab. Invest.* 32, 217–22 (1975); Eisenstein et al., *Amer. J. Pathol.* 81, 337–48 (1975); "Medical News", *JAMA* 232 (1), 14–15 (1975).; Brem and Folkman, *J. Exptl. Med.* 141, 427–39 (1975); and Kuettner et al., U.S. Pat. No. 4,042,457. These efforts are limited, of course, to the amount of TAF which is available and suitable for test purposes.

TAF finds further use in the development of tests such as an angiogenic assay or a diagnostic screening test for neoplasia. Klasbrun et al, *Cancer Res.* 36, 110–14 (1976); and Brem et al., *Science* 195, 880–81 (1977); *Cancer* 41, 239–44 (1978).

TAF also has been proposed as useful for wound healing. Rettusa et al, FASEB, Abstract No. 4309, 61st Ann. Meet., Apr. 1–8, 1977, Chicago, Ill.

Various human tumor cells have been reported heretofore as capable of elaborating TAF when measured by certain assays. Thus, extracts from human neuroblastoma, Wilms' tumor and human hepatoblastoma were found to contain TAF which was able to cause the formation of new blood vessels in the subcutaneous fascia of rats. Folkman et al., *J. Exptl. Med.* 133, 275–88 (1971).

So also, WI-38 embryonic lung SV W126 (SV 40 virus transformed W126), glioblastoma, meningioma and HeLa cells (the latter only in suspension culture and not in monolayers) grown in T-75 tissue culture flasks were described as giving a positive TAF response as measured by bioassay on the chick chorioallantoic membrane (CAM). Folkman and Klagsbrun, Chapter 31 of "Fundamental Aspects of Neoplasia", at page 402 (Gottlieb et al, eds.), Springer-Verlag, N.Y., 1975.

Subsequently, extracts from hypernephroma, haemangioma and human kidney were similarly described as eliciting a TAF response which resulted in the growth of new capillaries in the subcutaneous fascia of rats. Phillips et al., *Int. J. Cancer* 17, 549–58 (1976).

In still other experiments, Hubler and Wolf demonstrated TAF responses from human cutaneous melanoma implanted in transparent hamster-cheek-pouch membranes. *Cancer* 38, 187–92 (1976).

All of the foregoing tumor cells are derived from fresh tumors or primary cultures except the WI-38, SV W126 and HeLa cells. Fresh tumors and primary cultures are not, however generally suitable sources of TAF except for limited research purposes or small scale production. In order to provide a commercially significant source of TAF in terms of ready availability and adequate supply, production from a suitable established cell line is deemed necessary. As a practical matter the cell line should have not only specific TAF activity, but it should also have good cell growth characteristics in terms of rapid growth, good suspension growth, adaptability to large-scale culture and economical nutrient requirements.

The terms "cell line" and "established cell line" are used herein in conformance with the definitions published by Federoff in the *Tissue Culture Association Manual*, Vol. 1, No. 1, pp. 53–57 (1975).

DESCRIPTION OF THE INVENTION

Applicants have investigated numerous human tumor cell lines for the production of TAF, but most of them have been eliminated as unsuitable candidates in view of their poor growth characteristics as above-defined.

One cell line that has now been found to have good growth characteristics in suspension culture and is able to elaborate the desired TAF in suitable quantities is the human osteosarcoma cell line MG-63. The established cell line MG-63 was derived from an osteosarcoma by A. Billiau as reported by Billiau et al., *Antimicrob. Agents Chemother.* 12 (1), 11–15 (1977). Cultures of this cell line are available from A. Billiau, Rega Institute for Medical Research, Leuven, Belgium, and from the American Type Culture Collection, Rockville, Md., under the code designation ATCC CRL 1427. Although this cell line is described as useful for the production of interferon, it has not heretofore been known as a suitable source of TAF.

Initially, the medium used by applicants for maintenance and growth of this cell line was Dulbecco's modification of Eagle's minimum essential medium (MEM) containing 4 mg/ml of glucose. The culture medium was supplemented with 15% by volume fetal bovine serum without addition of any antibiotics, although lower concentrations of fetal bovine serum, for example, about 10–15%, also can be used. The cells were first grown at 37° C. in attached culture in 75 cm$^2$ T-flasks (Falcon Plastics) and were then converted to agitated, liquid suspension culture in the same medium in 4-liter and 100-liter vessels in accordance with the procedure described in U.S. Pat. No. 4,059,485. The cells were then harvested after 7 to 12 days growth since inoculation, and TAF was extracted and assayed according to the general procedures described in U.S. Pat. No. 4,059,486.

Specifically, the cells after growth were washed successively three times in lactated Ringer's solution, resuspended in phosphate buffered saline (pH 7–7.4) and stirred for 4 hours at 4° C. The supernatant after removal of the cells by centrifugation was retained as the cell extract. The cells pellet from the extract was resuspended in distilled water and stirred at 37° C. for 20 minutes. The supernatant after removal of the cell debris by centrifugation was retained as the cell lysate.

In various runs of 4 liters, and 100–110 liters the cell extracts and cell lysates were assayed to contain the following amount of total protein (Lowry protein assay):

| Run No. | Suspension Volume (Liters) | Time Since Inoculation (Days) | Total Protein | |
|---|---|---|---|---|
| 1 | 4 | 12 | 24.7 mg. | extract |
|   |   |   | 99.8 mg. | lysate |
| 2 | 4 | 10 | 8.4 mg. | extract |
|   |   |   | 116 mg. | lysate |
| 3 | 110 | 7 | 0.66 gm. | extract |
|   |   |   | 2.5 gm. | lysate |
| 4 | 110 | 7 | 0.52 gm. | extract |
|   |   |   | 1.0 gn. | lysate |

The cell extracts from the 4-liter runs gave strongly positive tests in the bioassay for TAF in the chorioallontoic membrane (CAM) of chick embryos, in accordance with the procedure described by Folkman, *Cancer Res.* 34, 2109–13; 36, 110–14 (1976).

The cell extracts from the 100- to 110-liter runs were subjected to further purification by CM-Sephadex ® (Pharmacia) chromatography and lyophilized. The purified material also gave a positive test in the CAM bioassay for TAF. The use of CM-Sephadex chromatography for obtaining a TAF active fraction from tumor cells is described by Tuan et al., *Biochemistry* 12 (17), 3159–65 (1973).

It will be appreciated that other nutrient culture media for culture of MG-63 cells can be used in place of Dulbecco's MEM, for example, any of the well-known tissue culture media described by H. J. Morton, *In Vitro* 6, 89–108 (1970). These conventional culture media contain known essential amino acids, mineral salts, vitamins and carbohydrates. They are also frequently fortified with mammalian sera such as fetal bovine serum. Suitable growth of the cells can be carried out at about 35°–38° C. but cell proliferation is best at 37° C. Growth under these cell culture conditions for about 4–8 days generally is sufficient to produce the desired TAF.

Other suitable equipment and procedures for growing cells in agitated, liquid suspension which can be adapted for culture of the cell line MG-63 will be readily apparent to the person skilled in the art by reference to well-known texts on cell culture such as, for example, Paul, "Cell and Tissue Culture," The Williams and Wilkins Company, Baltimore, 4th ed. 1970, at pages 277–291; Kruse and Patterson, "Tissue Culture Methods and Applications," Academic Press, New York, 1973, at pages 333–377.

It should also be understood that various means can be used to separate and purify TAF-containing fractions from the cells and cell culture product other than the illustrative specific recovery procedures described above. These various recovery means include the known techniques for the separation and purification of proteinaceous substances in general such as, for example, dialysis, salt and solvent precipitation, adsorption with gels, cellulose ion exchange chromatography, Sephadex gel filtration, electrophoresis, and lyophilization. Thus, TAF can be obtained by extraction from the cells followed by subjecting the extract to dialysis against NaCl (0.15 M), Sephadex G-100 chromatography, dialysis against water and lyophilization analogous to the methods described by Folkman et al., *J. Exptl. Med.* 133, 275–88 (1971) and Phillips et al., *Int. J. Cancer* 17, 549–58 (1976). According to Phillips et al., id, when the dialysate is subjected to chromatography on a column of Sephadex G-100 in 0.15 M NaCl, the fractions between 35,000 and 300,000 molecular weight contain the greatest TAF activity. According to Folkman, *Cancer Res.* 34, 2109–13 (1974), TAF is a proteinaceous substance having a molecular weight of approximately 100,000. It will be appreciated, however, that the aforesaid molecular weights are estimates based on partially purified TAF-containing products and the inventors are not bound by such estimates or by any particular purification procedure or TAF purity.

Various other examples will be apparent to the person skilled in the art after reading the present disclosure without departing from the spirit and scope of the invention. All such further examples are included within the scope of the appended claims.

What is claimed is:

1. Process for the production of human TAF in vitro comprising growing the human osteosarcoma cell line MG-63 in agitated, liquid suspension of nutrient culture medium at about 35°–38° C. for a sufficient time to elaborate TAF and isolating the resulting TAF from the cells or cell product.

2. The process of claim 1 in which the nutrient culture medium is Dulbecco's modification of Eagle's minimum essential medium.

3. The process of claim 1 in which the nutrient culture medium is fortified with mammalian serum.

4. The process of claim 1 in which the nutrient culture medium is fortified with from about 10% to about 15% fetal bovine serum.

5. The process of claim 1 in which the TAF is isolated by extraction from the cells.

6. The process of claim 1 in which the nutrient culture medium is Dulbecco's modification of Eagle's minimum essential medium and is fortified with fetal bovine serum and in which the TAF is isolated by extraction from the cells.

* * * * *